United States Patent [19]
Baura

[11] Patent Number: 6,016,445
[45] Date of Patent: Jan. 18, 2000

[54] METHOD AND APPARATUS FOR ELECTRODE AND TRANSTHORACIC IMPEDANCE ESTIMATION

[75] Inventor: Gail D. Baura, San Diego, Calif.

[73] Assignee: Cardiotronics, Carlsbad, Calif.

[21] Appl. No.: 08/632,878

[22] Filed: Apr. 16, 1996

[51] Int. Cl.[7] ............................. A61N 1/39; A61B 5/04
[52] U.S. Cl. ......................... 600/547; 607/8; 324/607
[58] Field of Search ................................. 128/734, 723; 607/8; 324/600, 607, 649, 663, 692; 379/30; 600/547

[56] References Cited

U.S. PATENT DOCUMENTS

| | | | |
|---|---|---|---|
| 4,328,808 | 5/1982 | Charbonnier et al. | 607/8 |
| 5,201,865 | 4/1993 | Kuehn | 607/8 |
| 5,215,081 | 6/1993 | Ostroff | 607/8 |
| 5,443,073 | 8/1995 | Wang et al. | 128/713 |
| 5,465,287 | 11/1995 | Egozi | 379/5 |
| 5,540,724 | 7/1996 | Cox | 607/8 |
| 5,558,671 | 9/1996 | Yates | 606/38 |
| 5,607,455 | 3/1997 | Armstrong | 607/8 |

*Primary Examiner*—Francis Jaworski
*Attorney, Agent, or Firm*—Morriss Bateman O'Bryant & Compagni

[57] ABSTRACT

Impedance across a load, such as a pair of face-to-face electrodes, or across electrodes in contact with a patient's chest cavity, respectively, is modeled as a resistor in series with a capacitor, wherein the reactance component of the impedance equals $2\pi*$frequency/capacitance. A reference square wave voltage is applied to the load in series with a selected load resistor, and a response voltage is measured across the load. Both the reference voltage and the response voltage are then used to estimate a transfer function between them. Equating this transfer function to a resistor-capacitor circuit model results in estimation of the actual resistance and capacitance components of the true impedance.

16 Claims, 6 Drawing Sheets

METHOD AND APPARATUS FOR ELECTRODE AND TRANSTHORACIC IMPEDANCE ESTIMATION

FIELD OF INVENTION

The present invention pertains generally to the field of electrical impedance estimation, including methods and apparatus for estimating electrode and transthoracic impedance in conjunction with non-invasive electrical cardiac therapy.

BACKGROUND

Defibrillation is the process of applying a strong electrical "countershock" to a patient's heart in an effort to convert an excessively fast heart rhythm—i.e., in order to slow and correct the heart rhythms and thereby allow the heart to pump more blood. A defibrillator is a device which applies such "countershocks." For example, "external" defibrillators produce and store energy for delivery to the heart through a pair of externally attached electrodes, wherein the actual delivered energy is a function of both the stored energy in the defibrillator device and the "transthoracic impedance" of the patient. Thus, for a given stored energy level, the transthoracic impedance determines the amount of current which flows to the myocardium of the patient. In particular, this current flow must be adequate to depolarize a critical mass of myocardium to achieve defibrillation.

The transthoracic impedance consists of two parts: the impedance due to the electrode-electrolyte interface at the connection site to the patient, hereafter referred to as "electrode impedance," and the impedance due to patient tissue. Impedance itself is comprised of two parts: resistance, which is constant, and reactance, which is frequency dependent. Historically, transthoracic and electrode impedance have been estimated using a method first proposed by Geddes in 1975. With this method, an "apparent" impedance is calculated as a ratio of peak voltage to peak current obtained when defibrillation energy is applied across a patient's chest, or, for purposes of testing patient electrodes, to face-to-face electrodes. As a variation of this method, Geddes showed that in dogs the ratio of peak voltage to peak current obtained from a high frequency (approximately 30 kHz) sinusoidal current approximates the ratio obtained from application of defibrillation energy.

Kerber later "validated" this approximation in 19 human subjects using a 31 kHz square wave voltage and a Hewlett Packard 78660 defibrillator, obtaining a mean impedance of 78.1±19.4Ω. In a paper describing these tests, Kerber used the description of "actual" impedance. However, this "actual" impedance, as calculated by Geddes and Kerber, assumes this impedance is a pure resistance, whereas the true impedance is not purely resistive, since it varies with frequency. Nevertheless, this method of impedance estimation has been used consistently for the past two decades to estimate transthoracic and electrode impedance. For example, Hewlett Packard has incorporated the high frequency ratio measurement in its defibrillators in the operation of a patient contact indicator, as described in U.S. Pat. No. 4,840,177.

Thus, it has been assumed since 1975 that the "apparent" impedance accurately estimates the true resistance. However, a simple experiment can be used to determine the accuracy of the apparent impedance ratio calculation, based on connecting the positive and negative outputs of a recently calibrated Hewlett Packard 43110 defibrillator directly to various resistors, each rated for 25 W, placed in series with a 50.6 $\mu$F capacitor, rated for 5 kV. For each resistor value, the apparent impedance, as estimated according to the Geddes/Kerber methodology, was measured from the mean of three measurements as:

| True Resistance (Ω) | "Apparent" Impedance (Ω) |
|---|---|
| 50.4 | 105 |
| 502 | 90 |
| 999 | 105 |

As can be observed from these figures, regardless of the true resistance value taken over a large resistive range, the measured apparent impedance is approximately constant. In other words, the apparent impedance method is predisposed to estimating resistance values of approximately 100Ω, even if the true resistance is an order of magnitude higher. In fact, Geddes himself has acknowledged the shortcomings of his measurement, stating, in a recent writing, that "in defibrillation studies many authors use the term impedance [Geddes' italics] to mean the ratio of peak voltage to peak current for the defibrillating current pulse, regardless of waveform. Although this practice violates the strictest definition of impedance, the ratio so obtained informs about the quality of the conducting pathway."

It is believed, however, that the Geddes/Kerber "apparent" impedance ratio may not, in reality, be providing sufficient information about the "quality of the conducting pathway," especially given the notable flaws in the underlying assumptions of this methodology pointed out by the above experiment. A significant need therefore exists for determining true electrode and transthoracic impedance. In particular, the true impedance estimate should consider both the resistance and reactance components of impedance, as opposed to a "lumped" resistance approach of Geddes/Kerber.

SUMMARY OF THE INVENTION

The present invention provides methods and apparatus for accurately estimating the actual electrode and/or transthoracic impedance, taking fully into account both the resistance and reactance components of impedance.

In a preferred embodiment, the actual impedance across a pair of face-to-face electrodes, or across electrodes in contact with a patient's chest cavity, respectively, is modeled as a resistor in series with a capacitor, wherein the "reactance" component of the impedance equals $2\pi*$frequency/capacitance. A reference square wave voltage is applied to the electrodes in series with a selected load resistor and a response voltage across the electrodes is measured. Both the reference voltage and the response voltage are then used to estimate a transfer function between them. Equating this transfer function to a resistor-capacitor circuit model results in estimation of the actual resistance and "capacitance" components of the true impedance.

An advantageous application of the present invention is that these true impedance measurements can be made within an external defibrillator connected to an electrode pair, e.g., for purposes of adjusting the stored energy level required to deliver a desired charge to a patient. In such preferred embodiments, an impedance measurement module is preferably isolated from any defibrillation energy or pacing current; e.g., by employing a high voltage relay. For example, if such a device is in "defibrillation mode", impedance is preferably measured every n heartbeats, where n is selected in accordance with a desired defibrillation algorithm and where the impedance measurement is halted if a defibrillation request is made by the operator. If such a device is in "pacing mode", impedance is preferably measured approximately once per minute, replacing no more than two pacing pulses. If such a defibrillator system were to display patient electrocardiogram ("ECG") waveforms on a patient monitor, as is common in the field, one or two previous ECG waveforms are preferably repeated across the display monitor during the impedance measurement in order to minimize changes in the defibrillator shock "advisory algorithms" and to prevent user confusion that may otherwise occur if the reference square wave voltage were to appear along with the ECG waveforms on the monitor.

As will be apparent to those skilled in the art, other and further objects and advantages will appear hereinafter.

BRIEF DESCRIPTION OF THE DRAWINGS

The drawings illustrate both the design and utility of preferred embodiments of the present invention, in which.

DETAILED DESCRIPTION OF THE ILLUSTRATED PREFERRED EMBODIMENT

Figure 1:
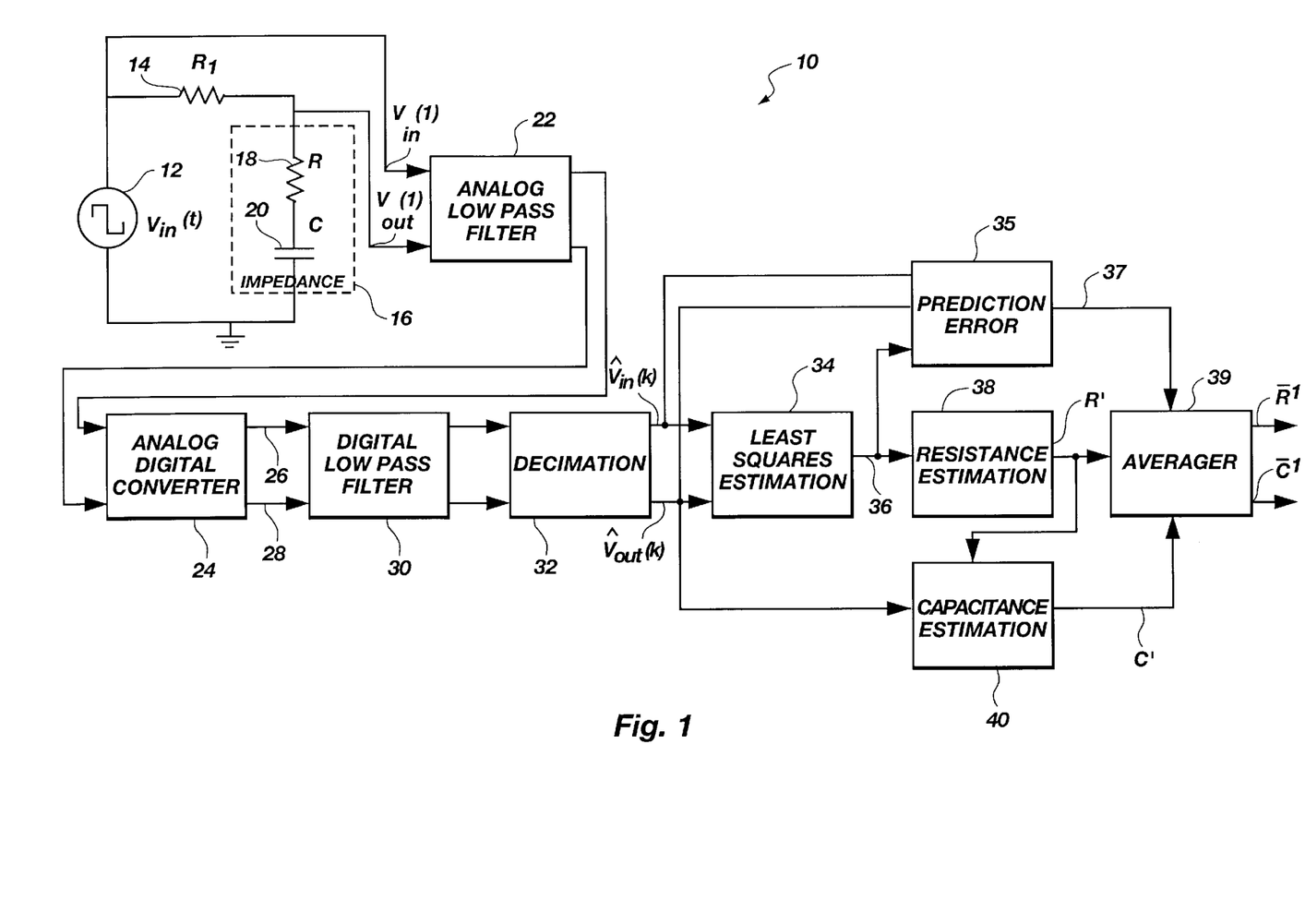
FIG. 1 is a functional block diagram of a preferred impedance estimation module in accordance with the present invention.

Referring to FIG. 1, a preferred impedance measurement module 10 includes a voltage source 12 providing a square wave input reference voltage $V_{in}(t)$ across a load resistor 14 in series with an "impedance load" 16 to be measured, such as, e.g., face-to-face electrodes (not shown) or electrodes applied to a patient's chest (not shown). In accordance with the present invention, the impedance load 16 is modeled as a resistor 18 in series with a capacitor 20, wherein an output voltage $V_{out}(t)$ is derived in response to the input reference voltage $V_{in}(t)$ being applied across the impedance load 16 and load resistor 14. The input voltage $V_{in}(t)$ and output voltage $V_{out}(t)$ are each passed through an analog low pass filter 22 to remove any (relatively) high frequency transient noise and respectively digitized by an A/D converter 24. In a preferred embodiment, the frequencies of the respective input voltage $V_{in}(t)$ and corresponding output voltage $V_{out}(t)$ are selected at approximately 1–2 Hertz, with the A/D converter 24 operating at less than or equal to 1000 Hertz. The "digitized" input voltage 26 and "digitized" output voltage 28 are then passed through a digital low pass filter 30 and (optionally) decimated 32, respectively, i.e., if necessary to obtain a more workable digital input voltage, $\hat{V}_{in}(k)$, and digital output voltage, $\hat{V}_{out}(k)$, respectively.

In a manner described in greater detail below, $\hat{V}_{in}(k)$ and $\hat{V}_{out}(k)$ are then used to estimate a transfer function between them, e.g., by employing a modeling technique such as least squares estimation 34. Model parameters 36 obtained from the least squares estimation 34 are then compared 38 to a transfer function between $V_{in}(t)$ and $V_{out}(t)$ obtained by circuit analysis in order to obtain the estimated resistance, R', of resistor 18. The estimated resistance R' is then used in a capacitance estimation calculation 40 in order to obtain the estimated capacitance, C', of capacitor 20 by analyzing the decay of $\hat{V}_{out}(k)$. The reactance portion of the impedance load 16 can then be determined, i.e., $2\pi f/C'$, where f is the frequency of the selected input voltage $V_{in}(t)$. The total true impedance (in ohms) across load 16 can thus be estimated by adding the resistance and reactance portions: $R'+2\pi f/C'$.

In a preferred embodiment, $V_{in}(t)$, $V_{out}(t)$ and the model parameters 36 from the least squares estimation 34 are also used to synthesize an estimate of $\hat{V}_{out}(k)$, wherein this estimate is then compared to the actual $\hat{V}_{out}(k)$ in a prediction error analysis 35 order to obtain a measure of prediction error 37. R' and C' are then preferably averaged 39 with several values taken over a selected sample time period, preferably using the prediction error 37 as a guide for discarding suspect values from the averaging process 39, in order to obtain a more accurate reading of the impedance across load 16,—i.e., by using the averaged values, $\overline{R}'$ and $\overline{C}'$, respectively, over the sample period. A more detailed description of the functional operation of the above-identified impedance measurement module 10 follows. It will be recognized by one of ordinary skill in the art that the described functions and operations can be performed, e.g., by a programmed microprocessor in conjunction with one or more look-up memory tables (not shown).

In particular, the transfer function between $V_{in}(t)$ and $V_{out}(t)$, which is equivalent to the transfer function between $\hat{V}_{in}(k)$ and $\hat{V}_{out}(k)$, respectively, can be derived from the following circuit analysis (where the load resistor 14 is designated as $R_1$):

Using voltage division and Laplace domain representation, $$V_{out}(s) = V_{in}(s) R + \frac{\frac{1}{sC}}{R + \frac{1}{sC} + R_1} \quad (1)$$

Rearrangement yields the transfer function:

$$\frac{V_{out}(s)}{V_{in}(s)} = \frac{R + \frac{1}{sC}}{R + \frac{1}{sC} + R_1} \quad (2)$$

Using the bilinear transformation, $s=(z-1)/(z+1)$, to convert to the z domain results in:

$$\frac{V_{out}(z)}{V_{in}(z)} = \frac{\frac{R + \frac{1}{C}}{R + R_1 + \frac{1}{C}} + \frac{\frac{1}{C} - R}{R + R_1 + \frac{1}{C}} z^{-1}}{1 + \frac{\frac{1}{C} - R - R_1}{R + R_1 + \frac{1}{C}} z^{-1}} \quad (3)$$

Several known models can also be used to estimate this transfer function, including a standard autoregressive moving average ("ARMA") model, wherein:

$$V_{out}(k) = -a_1 V_{out}(k-1) + b_0 V_{in}(k) + b_1 V_{in}(k-1) \quad (4)$$

Transformation to the z domain yields:

$$V_{out}(z) = -a_1 z^{-1} V_{out}(z) + b_0 V_{in}(z) + b_1 z^{-1} V_{in}(z) \quad (5)$$

Rearrangement yields the transfer function:

$$\frac{V_{out}(z)}{V_{in}(z)} = \frac{b_0 + b_1 z^{-1}}{1 + a_1 z^{-1}} \quad (6)$$

Equating this transfer function to the transfer function obtained by circuit analysis yields:

$$R = \frac{(b_0 - b_1) R_1}{2(1 - b_0)} \quad (7)$$

Although C can also be obtained from these transfer functions, it is preferably not determined in this manner, as there is not sufficient resolution for accurate capacitance estimates on the order of $10^{-5}$ farads.

In the illustrated preferred embodiment, the ARMA model parameters 36 are obtained using least squares estimation ("LSE") 34. As its name implies, this technique estimates the model parameters 36 by minimizing the squared difference between observed and calculated data from an assumed model. To derive the LSE equations, the following terms are defined:

"period" = number of samples per waveform (8)

$$\hat{V}_{in}^T = [\hat{V}_{in}(k) \ \hat{V}_{in}(k+1) \ \ldots \ \hat{V}_{in}(k+\text{period})] \quad (9)$$

$$\hat{V}_{out}^T = [\hat{V}_{out}(k) \ \hat{V}_{out}(k+1) \ \ldots \ \hat{V}_{out}(k+\text{period})] \quad (10)$$

$$\phi = \begin{bmatrix} \hat{V}_{out}(k-1) & \hat{V}_{in}(k-1) & \hat{V}_{in}(k-2) \\ \vdots & & \vdots \\ \hat{V}_{out}(k+\text{period}-1) & \hat{V}_{in}(k+\text{period}-1) & \hat{V}_{in}(k+\text{period}-2) \end{bmatrix} \quad (11)$$

$$\theta = [a_1 \ b_0 \ b_1] \quad (12)$$

Using these terms, the squared difference between observed and calculated data is:

$$\text{Cost}(\theta) = [\hat{V}_{out} - \phi \theta]^2 \quad (13)$$

From calculus, this difference function is minimized when its derivative is set to zero:

$$\frac{\delta \text{Cost}(\theta)}{\delta \theta} = 0 = -2\phi^T \hat{V}_{out} + 2\phi \phi^T \theta \quad (14)$$

Rearranging yields an equation for calculating model parameters:

$$\theta = [\phi^T \phi]^{-1} \phi^T V_{out} = [a_1 \ b_0 \ b_1] \quad (15)$$

Figure 2:
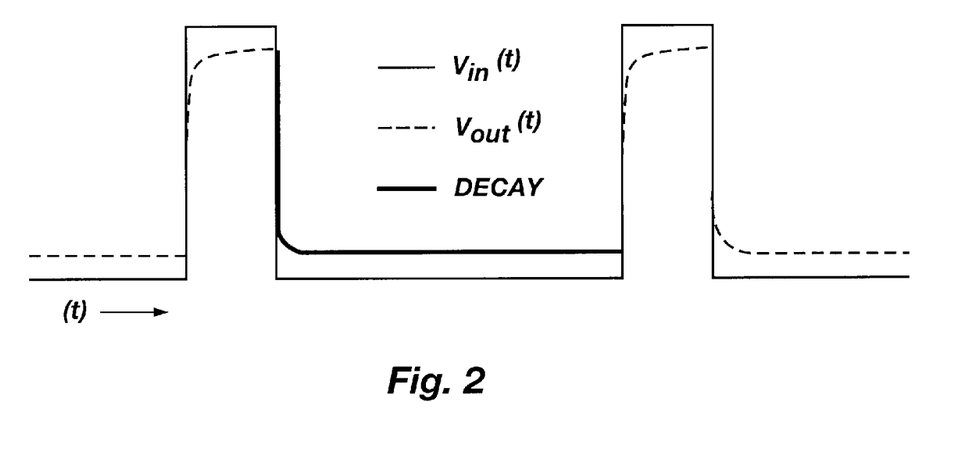
FIG. 2 is an illustration of the voltage waveform decay used to estimate capacitance in the preferred impedance estimation module of FIG. 1.

Once the estimated R' has been determined from ARMA model parameters, i.e., by inserting the derived model parameter values 36 in equation (7), it is then used as an input to the capacitance estimation calculation 40. In particular, capacitance is estimated by fitting the decay of $\hat{V}_{out}(k)$, in response to the low portion of the square wave voltage $\hat{V}_{in}(k)$. Because the impedance across load 16 is assumed to be a resistor 18 in series with a capacitor 20, this decay can be fit to an exponential of form $e^{-k/RC}$, i.e., $e^{-k/(R+R_1)C}$ for the impedance measurement module 10 depicted in FIG. 1. An illustration of this decay, in unfiltered $V_{out}(t)$, is shown in FIG. 2.

To estimate capacitance, the squared error between the observed and calculated decay is preferably minimized. Known optimization techniques can be employed for this minimization, including Powell's Successive Quadratic Estimation. Assuming that the squared error is a unimodal function that is continuous over an interval, the squared error can be approximated by a quadratic polynomial based on three capacitor samples $c_0$, $c_1$ and $c_2$, as follows:

$$\text{decay\_error}(C) = d_0 + d_1(C - c_0) + d_2(C - c_0)(C - c_1) \quad (16)$$

Substituting $c_0$, $c_1$ and $c_2$, respectively, yields values of $d_0$, $d_1$ and $d_2$, where:

$$d_0 = \text{decay\_error}(c_0) \quad (17)$$

$$d_1 = \frac{\text{decay\_error}(c_1) - \text{decay\_error}(c_0)}{c_1 - c_0} \quad (18)$$

$$d_2 = \frac{1}{c_2 - c_1} \left( \frac{\text{decay\_error}(c_2) - \text{decay\_error}(c_0)}{c_2 - c_0} - \frac{\text{decay\_error}(c_1 - \text{decay\_error}(c_0)}{c_1 - c_0} \right) \quad (19)$$

Assuming this quadratic is a good approximation of the squared error, it can then be used to find the minimum error by setting the first derivative to zero:

$$\frac{\delta \text{decay error}(C)}{\delta C} = d_0 + 2 d_1 C - d_1 c_0 - d_1 c_0 = 0 \quad (20)$$

Rearranging yields an estimate of capacitance:

$$C' = \frac{c_0 + c_1}{2} - \frac{d_1}{2 d_2} \quad (21)$$

Figure 3:
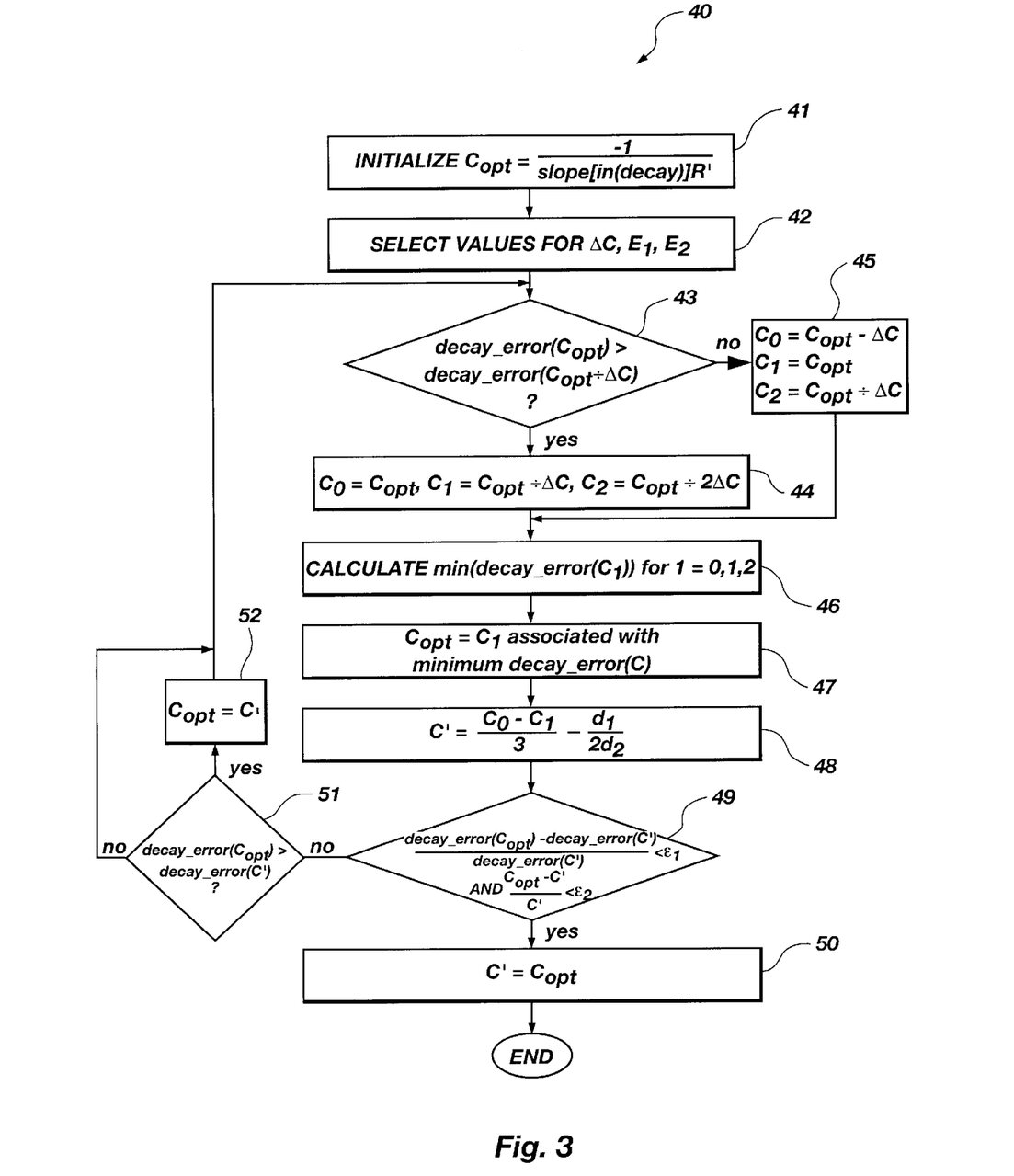
FIG. 3 is a flow chart detailing a preferred capacitance estimation algorithm employed in the preferred impedance estimation module of FIG. 1.

The preferred capacitance estimation algorithm is illustrated in FIG. 3, wherein the following steps are carried out:

Step 41: To initiate the capacitance estimation calculation 40, an initial capacitance is determined by taking the natural log of the decay function $e^{-k/(R+R_1)C}$, estimating its slope, m, and calculating $C_{opt} = -1/m(R'+R_1)$, respectively.

Step 42: A value of capacitance step size, $\Delta C$, e.g., in a preferred embodiment, $5 \times 10^{-6}$, and values of convergence parameters, $\epsilon_1$ and $\epsilon_2$, e.g., in a preferred embodiment, 0.75 and 0.005, respectively, are selected.

Step 43: The decay_error(C) for $C_{opt}$ and $(C_{opt} + \Delta C)$ are then calculated.

Step 44: If the "decay_error($C_{opt}$)" is greater than the "decay_error($C_{opt} + \Delta C$)", the $c_i$ are defined as $c_0 = C_{opt}$, $c_1 = (C_{opt} + \Delta C)$, and $c_2 = (C_{opt} + 2\Delta C)$.

Step 45: If the "decay_error ($C_{opt}$)" is less than or equal to the "decay_error ($C_{opt} + \Delta C$)", the $c_i$ are defined as $c_0 = (C_{opt} - \Delta C)$, $c_1 = C_{opt}$, and $c_2 = (C_{opt} + \Delta C)$.

Step 46: The minimum decay_error($c_i$); for $c_0$, $c_1$ and $c_2$ is determined.

Step 47: The $c_i$ value corresponding to this minimum is equated to $C_{opt}$.

Step 48: C' is then calculated from equation (21).

Step 49: If [decay_error($C_{opt}$)−decay_error(C')]/ [decay_error(C')] is less than or equal to $\epsilon_1$, and if ($C_{opt}$−C')/C' is less than or equal to $\epsilon_2$, respectively, the algorithm terminates (50), with C' as calculated in Step 48.

Otherwise:

Step 51: If decay_error($C_{opt}$) is greater than decay_error (C'), then $C_{opt}$ is redefined as $C_{opt}$=C' (52); otherwise, $C_{opt}$ remains as calculated in Step 47. The algorithm then loops back to Step 43.

Once the respective resistance and capacitance estimates R' and C' have been calculated, they are sent to the averager 39. The averager 39 also requires a third input, prediction error value 37. Preferably, "prediction error" is defined as the squared error between the observed data, i.e., the $\hat{V}_{out}(k)$ waveform, and the calculated data, i.e., the ARMA model $\hat{V}_{out}(k)$ waveform. However, alternate measurements that normalize this error or emphasize specific waveform features can also be used. The averager 39 preferably utilizes the prediction error 37 to monitor the level of system noise and to determine if the current estimates of R' and C'—i.e., each estimated $\overline{R}$' and $\overline{C}$' within a sample period—should be averaged with the past estimates or discarded. The exact construction of the averager 39 is preferably determined by an algorithm designer, e.g., during analysis of clinical data, depending on the particular data and being analyzed and selected error criteria. Once all of the non-excluded values of R' and C' over a sample period have been averaged, the averager 39 outputs $\overline{R}$' and $\overline{C}$', respectively, from which the true impedance across the given load 16 can be estimated.

As can be observed, given the foregoing teachings, the impedance estimation techniques of module 10 could be used as a stand alone impedance measurement system, or could be incorporated into another device or system, such as an external defibrillator system.

Figure 4:
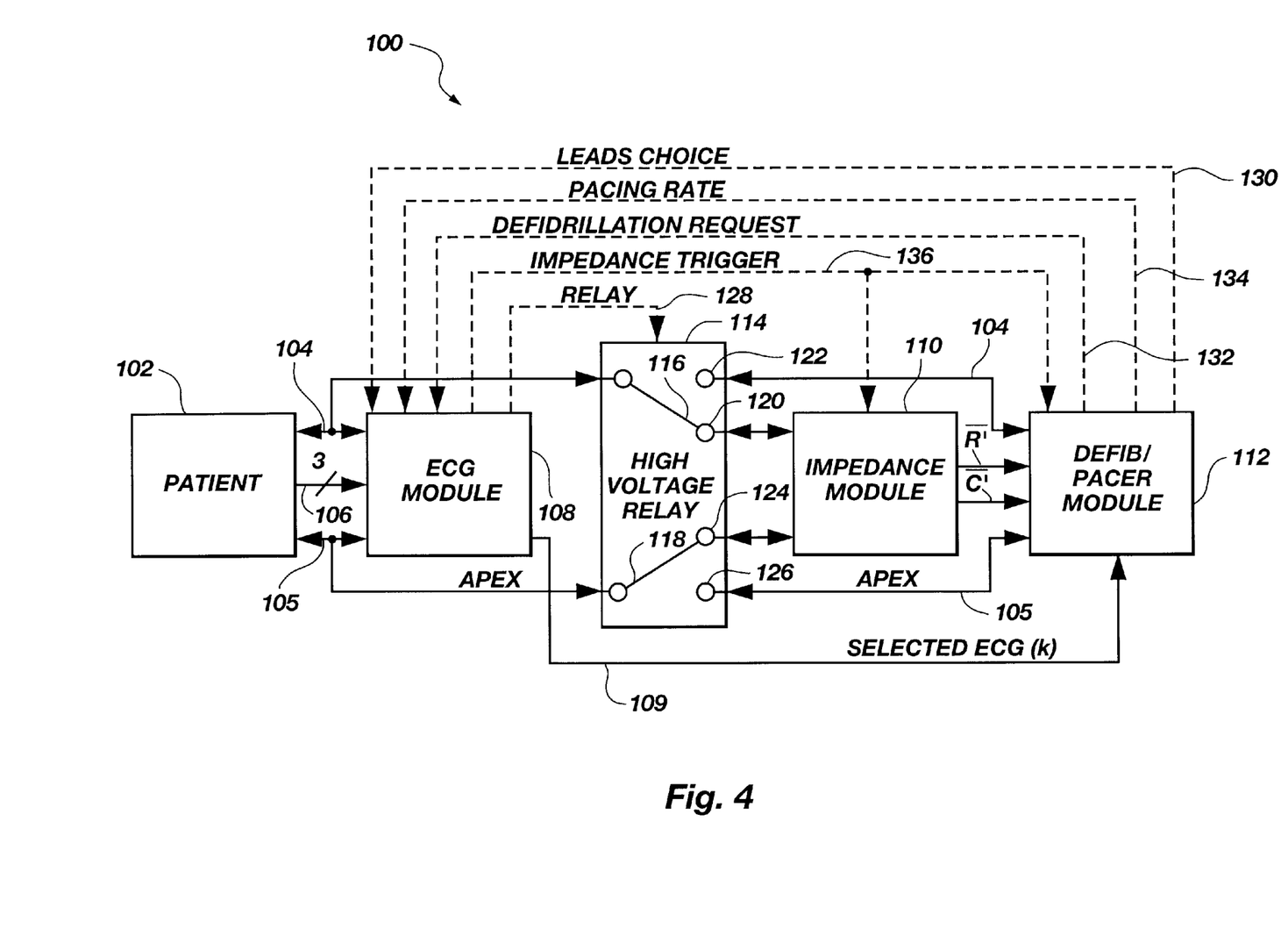
FIG. 4 is a functional block diagram of a preferred arrangement for employing the impedance estimation module of FIG. 1 within an external defibrillator system, including an ECG waveform display module.

Referring to FIG. 4, an external defibrillator system 100 employing an impedance estimation module 110 substantially similar to the aforedescribed impedance estimation module 10, delivers defibrillation energy and/or electrical pacing therapy from a defibrillator/pacer module 112 to a patient 102 by way of an external electrode cable pair, including a sternum electrode cable 104 and an apex electrode cable 105, respectively. For monitoring purposes, the electrode cables 104 and 105, along with each cable of a three-cable ECG connection 106, respectively, are also connected to an ECG module 108. The ECG module 108 receives patient heart signals from a selected pair of electrode or ECG cables 104/105/106, i.e., based on a "leads choice" instruction signal 130 from the defibrillator/pacer module 112, and converts the received signals into an EĈG(k) waveform signal. The EĈG(k) waveform signal is then transmitted 109 to the defibrillator/ pacer module 112, for display on a patient monitor (not shown).

A high voltage relay 114 allows for alternate electrical connection between the patient electrode cables 104/105 and either the impedance module 110, or the defibrillator/pacer module 112, respectively. Although many known switch configurations may be successfully employed in conjunction with the depicted preferred embodiment, the illustrated high voltage relay 114 comprises a pair of switches 116 and 118, which operate in tandem to selectively connect patient electrode cables 104/105 in the following manner: Switch 116 alternately connects the sternum electrode 104 with the impedance module 110 via switch position 120, or the defibrillator/pacer module 112 via switch position 122, respectively. Switch 118 alternately connects the apex electrode 105 with the impedance module 110 via switch position 124, or the defibrillator/pacer module 112 via switch position 126, respectively.

A relay control signal, or "relay flag" 128 from the ECG module 108 controls the position of switches 116 and 118. When the relay flag 128 is "high", the respective switches 116 and 118 are set to positions 120/124, thereby connecting the electrode cable pair 104/105 to the impedance module 110 (as depicted in FIG. 4). Conversely, when the relay flag 128 is "low", respective switches 116 and 118 are set to positions 122/126, thereby connecting the electrode cable pair 104/105 to the defibrillator/pacer module 112.

When a defibrillation charge is to be delivered-to the patient 102, a "defibrillation request" flag 132 is sent from the defibrillator/pacer module 112 to the ECG module 108. The ECG module sets the relay flag 128 to "low", connecting the electrode cable pair 104/105 to the defibrillator/pacer module 112, whereby the defibrillation energy may be delivered to the patient without harming the impedance measurement module 110, or otherwise having an extraneous electrical path through the module 110 interfere with the defibrillating current. Likewise, to deliver an ongoing pacing signal to the patient 102, the relay flag 128 is kept on "low".

As noted above, the delivery of the defibrillation and/or pacing therapies are preferably facilitated by taking periodic patient impedance measurements, e.g., to ascertain whether the optimal defibrillation charge is being delivered, or to check on the integrity of the patient-electrode connections, etc. For example, if the defibrillator system 100 is in a "defibrillation mode"—i.e., when preparing for, delivering, or observing the results of, respectively, a defibrillation charge—the transthoracic impedance is preferably measured every n heartbeats, where n is selected in accordance with a desired defibrillation algorithm employed by the system operator, depending on the particular patient therapy requirements. If the defibrillator system 100 is in "pacing mode"—i.e., where an electrical "pacing" pulse is delivered to control the patient's heartbeat rhythm—the transthoracic impedance is preferably measured approximately once every minute, preferably replacing no more than two pacing pulses during a measurement period.

As described in greater detail below, to measure the transthoracic impedance, the ECG module 108 sets relay flag 128 to "high", and sends an "impedance trigger" flag 136 to the impedance module 110, thereby initiating an impedance measurement cycle. The impedance module 110 then applies a square wave reference voltage $V_{in}(t)$ to sternum and apex lines 104/105, measures the responsive output voltage $V_{out}(t)$, and, in a manner described above, calculates the estimated average resistance portion, $\overline{R}$', and "capacitance" portion, $\overline{C}$', respectively of the patient's transthoracic impedance over the measurement period. The values for $\overline{R}$' and $\overline{C}$' are then transmitted directly to the defibrillator/pacer module 112, where the true impedance is used, e.g., in adjusting the level of the ensuing defibrillation charge to be delivered to the patient 102.

Because the square wave $V_{in}(t)$ used for impedance measurement will be received by the selected patient monitoring leads, (i.e., over cables 104/105/106), the ECG module 108 preferably re-transmits the most recent one or two EĈG(k) waveforms to the defibrillator/pacer module 112 during the impedance measurement period. The "repeat" waveform(s) are displayed on the patient monitor instead of the current EĈG(k) signal, which will be grossly distorted by the impedance measurement voltage $V_{in}(t)$. Further, this "bypass" may be critical if defibrillation shock advisory algorithms based on the output EĈG(k) signal 109 are used by the defibrillation/pacer module 112 to decide, or assist in the decision, of when to send a defibrillation charge—i.e., the repeat of the immediately previous waveform(s) will prevent the impedance measurement process from inadvertently triggering an unwanted defibrillation charge delivery. Notably, if the system operator requests a defibrillation charge be delivered during the (albeit relatively brief) impedance measurement period, the ECG module will immediately reset the relay flag 128 to "low".

With respect to a preferred duration for an impedance measurement period, which will influence the number of R' and C' measurements available for averaging, it is important that such period not adversely impact on a patient's ongoing pacing therapy. For example, of three more common external defibrillator/pacer systems, including Hewlett Packard's "Codemaster", Physio Control's "Likepak 9" and Zoll's "PD1400", respectively, the Hewlett Packard Codemaster possesses the most stringent pacing specification of ±2 pulses per minute at the maximum rate of 180 pulses per minute. Thus, by limiting the impedance measurement interval to within the time interval of two pacing pulses, the pacing accuracy specification is still met when two pacing pulses are omitted.

In particular, to adhere to Hewlett Packard's pacing accuracy specification, the impedance measurement must be completed within 0.67 seconds. Assuming a square wave pulse duration of 0.2 seconds, the measurement time interval is merely a function of the voltage response decay. Robust resistance and capacitance estimation requires that the decay curve decreases significantly. Using circuit analysis of the aforedescribed preferred embodiment of FIGS. 1 and 2, this decay decreases to 86% its original value at two times the circuit time constant, or two times the total resistance times capacitance. The total resistance is the sum of the impedance (i.e., "patient") resistance and R. Assuming a maximum patient resistance of 4000Ω and a maximum capacitance of 50 μF, the worst case load resistance is:

$$R_{1,ext.defib} = \frac{\text{time interval} - \text{pulse duration}}{2C} - R = 700\,\Omega \tag{22}$$

Therefore, when the preferred impedance module 10 is employed within an external defibrillator system, e.g., as is module 110 in FIG. 4, it is preferred that a load resistor 14 of at most 700Ω is used in order to insure the impedance measurement can be completed with 0.67 seconds.

While it is desirable to concurrently estimate impedance and perform defibrillation and/or pacing therapy, this is not readily accomplished because the frequencies of the input square wave voltage $V_{in}(t)$ and the ECG signal(s) overlap. As previously stated, robust resistance and capacitance estimation requires that the decay curve decrease to baseline, resulting in a square wave frequency of approximately 1 Hz for estimating maximum patient resistance and capacitance values. In contrast, current external defibrillators rely on waveforms of approximately 30 kHz for impedance estimation during defibrillation/pacing, i.e., using the "apparent" impedance method of Geddes. This approach has been workable, since a 30 kHz waveform is easily separated from an ECG of approximately 1 Hz using standard filtering techniques, and does not generate patient discomfort.

To insure that the preferred characteristics of the reference voltage $V_{in}(t)$ do not generate any undue patient discomfort, a trial was performed, wherein a 2 volt peak-to-peak, 1 Hz square wave with pulse duration 0.2 seconds and a mean current amplitude of 0.5±0.09 mA peak-to-peak, was applied across a 1990Ω resistor in series with R2 616 electrodes adhered in the anteriolateral position to the chest of ten male and ten female subjects. The subjects had a mean age 34±8 years and a mean body weight of 176±39 lb. Up to 10 V peak-to-peak was applied. Eleven of the subjects did not perceive any current at this maximum voltage level (2.6±0.4 mA). For the remaining nine subjects (2 male, 7 female), the mean threshold for a perceptible current "tapping" was 1.9±0.4 mA. Further, for the subjects who did perceive a current flow, the perceptible current threshold was not correlated with age, weight, resistance, or capacitance, as analyzed by linear regression.

Figure 5:
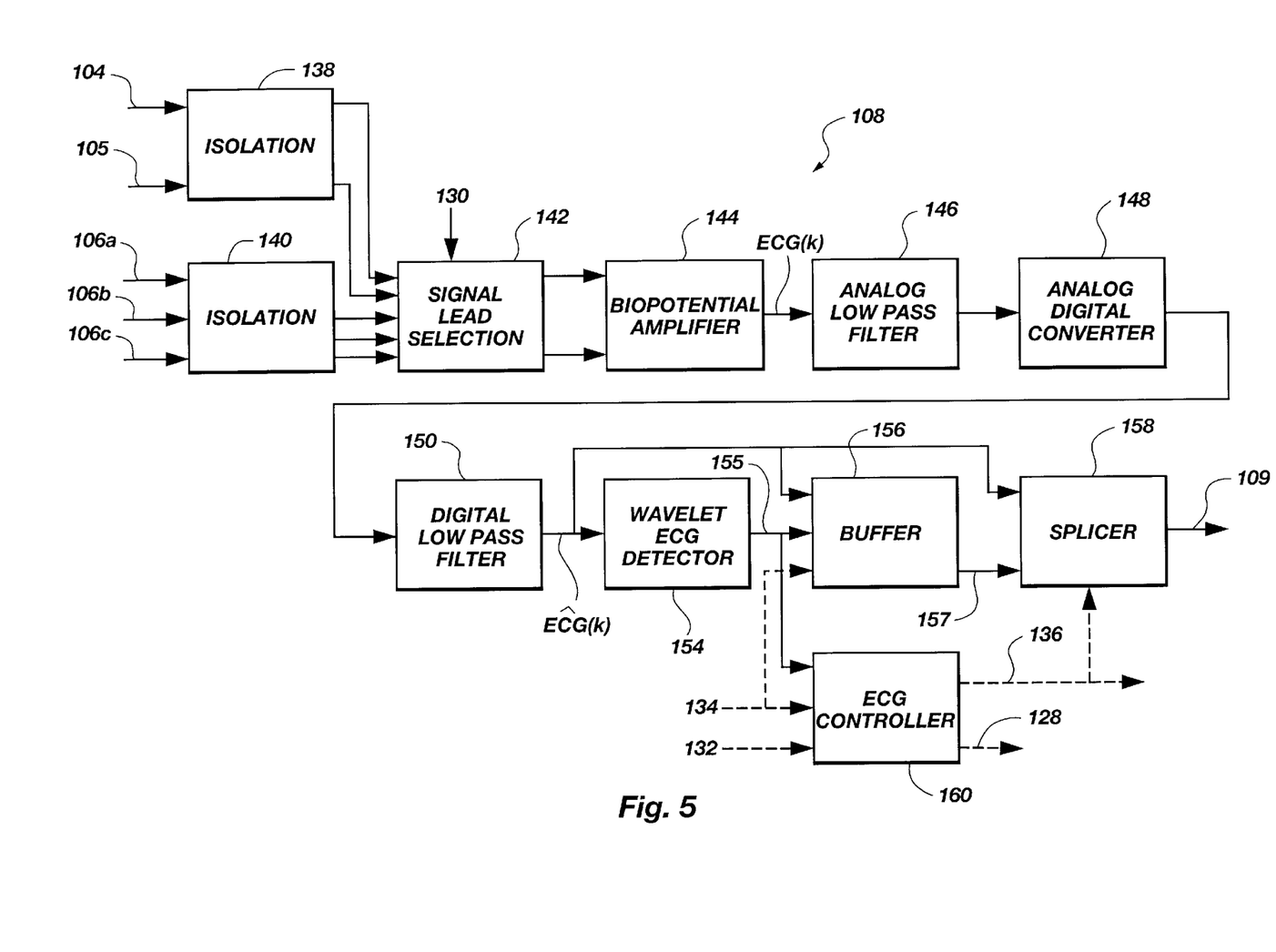
FIG. 5 is a functional block diagram of a preferred embodiment of the ECG module of the defibrillator system of FIG. 4.

A more detailed description of the function features and operation of a preferred ECG module 108 is as follows:

Referring to FIG. 5, isolation 138 is preferably provided between the sternum and apex electrodes and the ECG module 108, i.e., interposed before the connection of the respective electrode cables 104 and 105 to module 108, in order to protect the ECG module 108 from high input currents, e.g., generated during a defibrillation procedure. Electrical isolation 140 is also preferably provided at the inputs of the ECG connection is cables 106, which include a left arm ("LA") cable 106a, right arm ("RA") cable 106b and left leg ("LL") cable 106c, respectively. After passing through isolation 138 and 140, respectively, signals carried over two of the five respective patient cables, i.e., 104, 105, 106a, 106b or 106c, are selected 142 based on the leads choice signal 130 from the defibrillator/pacer module 112 for generating an ECG waveform signal of the patient's heart rhythm. The selected patient signals are input into a biopotential amplifier 144, which outputs an analog signal, ECG(t), representing the difference in voltage potential between the two selected input leads. In particular, each patient heartbeat period is associated with a new "waveform" (or "waveform period"), wherein the ECG(t) signal comprises a series of successive corresponding output waveforms.

The analog patient ECG signal ECG(t) is preferably passed through an analog low pass filter 146, digitized 148 and passed through a digital low pass filter 150, respectively, to thereby obtain a digital representation of the patient ECG signal, EĈG(k). The EĈG(k) signal is then transmitted from the digital filter 150 through a splicer 158, which, except during an impedance measurement period, allows the current EĈG(k) signal to pass through directly to the defibrillator/pacer module 112. The EĈG(k) signal is simultaneously fed from filter 150 into both a wavelet ECG detector 154 and a buffer 156, respectively. The wavelet ECG detector 154 detects the onset of each waveform period within the EĈG(k) signal and generates a corresponding "period onset" timing signal 155.

Period onset is preferred rather than, e.g., QRS complex or R wave detection, as it is only necessary to detect an occurrence of each EĈG(k) period, but not necessarily the commencement of the R wave. While the period onset of each EĈG(k) waveform can be determined using many methods, the wavelet transform method is preferred because it more easily distinguishes sharp waveform variations, even when severe noise distortion is present.

By definition, a wavelet is any function whose integral is equal to zero. Typically, a wavelet is scaled using a scale factor, g, which for the dyadic wavelet results in:

$$h_g(t) = \frac{1}{2^g} h\left(\frac{t}{2^g}\right) \tag{23}$$

The wavelet transform of a function, f(t), is just the convolution of the wavelet with this function.

For ECG detection, the wavelet used is preferably a quadratic spline, dyadic wavelet, as per Kadambe et al. The Fourier transform of this wavelet is:

$$F\{h_g(t)\} = \begin{cases} \dfrac{j}{2^g}\dfrac{w}{2^g}\left[\dfrac{\sin\left(\dfrac{1}{4}\cdot\dfrac{w}{2^g}\right)}{\dfrac{1}{4}\cdot\dfrac{w}{2^g}}\right]^4 e^{3j\frac{w}{2^g}}, & 1 \le w \le 199 \\ 0, & \text{otherwise} \end{cases} \quad (24)$$

where $j=\sqrt{-1}$.

Using a scale factor g=1, the wavelet transform is:

$$W(k) = \sum_{i=1}^{199} E\hat{C}G(k=i)\text{Re}\{h_1(i)\} \quad (25)$$

Because the form of this waveform transform is recursive, it can be calculated in real time with every incoming $E\hat{C}G(k)$ sample, wherein the period offset is defined as the local maxima obtained every period, i.e., which is phase shifted from the R wave.

The buffer memory 156 continuously stores one or more of the most current ECG waveforms received from the filter 150, using the onset timing signal 155 to monitor when each new waveform period begins and ends, respectively. The stored waveforms 157 are then fed (in the same order) into the splicer 158, with an effective delay equaling the number of stored waveforms. In other words, if one waveform is stored in buffer 156, it is sent to the splicer 158 with a delay of one waveform period (i.e., immediately after it was originally sent from the filter 150). If two waveforms are stored in buffer 156, the stored waveforms 157 arrive at the splicer 158 with a delay of two waveform periods, etc. Except during an impedance measurement period, the splicer 158 discards the delayed $E\hat{C}G(k)$ waveform(s) 157, allowing the current $E\hat{C}G(k)$ waveforms to pass through to the defibrillator/pacer module 112. However, when an impedance measurement is taking place, the splicer 158 transmits (i.e., "replays") the delayed waveforms 157 to defibrillator/pacer module 112 in place of the current waveforms.

When the system is in "pacing mode," the number of "stored" waveforms is preferably based on the actual pacing rate 134, which is supplied from the defibrillator/pacing module 112 to the buffer 156. As was previously indicated, it is preferable that no more than two pacing periods be disrupted during an impedance measurement period. As such, no more than the two most recent waveform periods would be required to be stored in the buffer 156. Preferably, a simple algorithm based on the actual pacing rate 134 is employed,—e.g., by way of example only: "store one waveform period if the pacing rate is $\le 80$ beats per minute, else store two waveform periods." When there is no pacing, but the patient's ECG waveforms are still being displayed, as may be the case, e.g., when the system is in "defibrillation mode," the number of stored waveforms in buffer 156 is determined by the measurement period resulting from the selected impedance measurement algorithm of the system operator; i.e., wherein the number of required waveforms to be stored in buffer 156 depends directly on how many are required to cover the duration of the impedance measurement period.

In the illustrated preferred embodiment, an ECG controller 160 monitors the period onset signal 155, pacing rate 134, and defibrillation request flag 132, respectively. The controller 160 also controls the impedance measurement flag 136 and the relay flag 128, respectively. Unless an impedance measurement period is called for, both the impedance trigger flag 136 and the relay flag 128 remain set to "low". If the pacing rate is "zero," (e.g., during "defibrillation mode"), the ECG controller 160 counts the number of period onsets in signal 155 and sets the impedance trigger 136 to "high" every n waveforms, depending on the desired impedance measurement frequency, preferably at least once per minute. Similarly, if the pacing rate is non-zero, (i.e., during "pacing mode"), then the impedance trigger is preferably set to "high" when either n=(pacing rate-1), or n=(pacing rate-2) waveforms are counted. Preferably, the period onset signal 155 not only controls the timing of the storage of each new $E\hat{C}G(k)$ waveform in buffer 156, but is also used by the ECG controller 160 to determine the exact timing for setting the impedance trigger flag 136 to "high"—i.e., to correspond with the beginning of a new ECG waveform period onset—upon reaching the nth waveform. If the defibrillation request flag 132 is set to "high," the ECG controller 160 immediately sets the impedance trigger flag 136 and relay flag 128 to "low," even if an impedance measurement period is prematurely terminated.

In particular, when set to "high", the impedance trigger flag 136 is used to simultaneously trigger the start of an impedance measurement period (at module 110) and to cause the splicer 158 to switch its selected output $E\hat{C}G(k)$ signal 109 to from the current $E\hat{C}G(k)$ signal to the delayed $E\hat{C}G(k)$ signal 157 for the duration of the impedance measurement period, e.g., one or two waveform periods, at which point the splicer 158 will automatically revert to outputting the current $E\hat{C}G(k)$ signal. Because the baseline "offsets" of the current and delayed $E\hat{C}G(k)$ signals may differ, the splicer 158 preferably compensates for these offsets to make the data appear continuous on the monitor.

For example, an internal counter (not shown) can be provided within the splicer 158 that resets to zero at every period onset. When the impedance trigger flag 136 is set to "high", the splicer 158 adds the following offset ("offset0") to the "splice" of stored $E\hat{C}G(k)$ data before transmitting it to the defibrillator/pacer module 112:

$$\text{offset0} = \text{current } E\hat{C}G(-1) - \text{stored } E\hat{C}G(0) \quad (26)$$

When the splicer first switches back to transmitting current $E\hat{C}G(k)$, it adds the following offset ("offset1"):

$$\text{offset1} = \text{stored } E\hat{C}G(p-1) - \text{current } E\hat{C}G(p) + \text{offset0} \quad (27)$$

where "p" equals the length of the stored $E\hat{C}G(k)$ waveform array and, as such, the number of samples until the next period onset.

Figure 6:
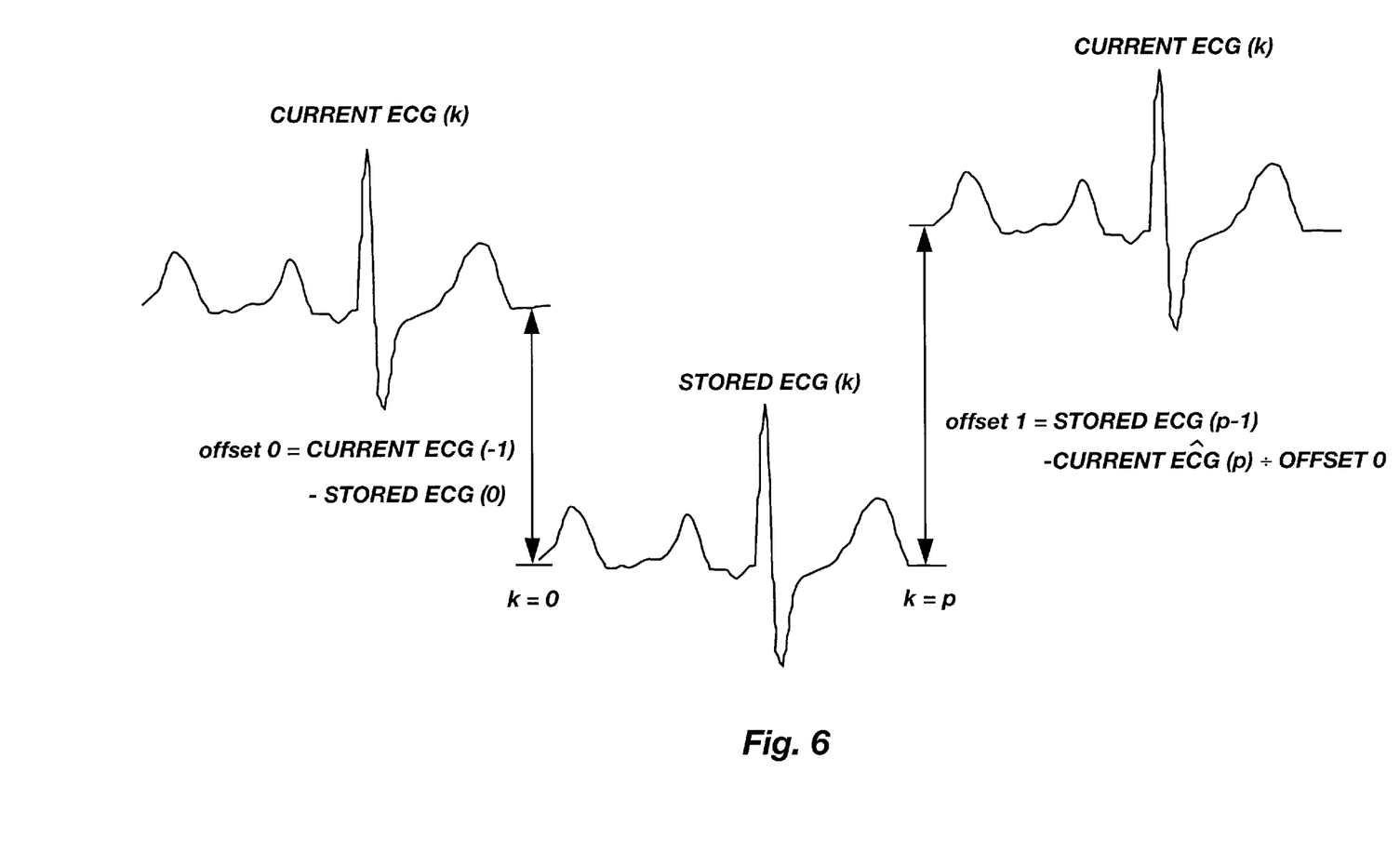
FIG. 6 is an illustration of an exemplary ECG waveform display employing a preferred splicing technique provided by the ECG module of FIG. 5.

With each current $E\hat{C}G(k)$ sample thereafter, the splicer 158 increments or decrements offset1 by a small value (such as $10^{-6}$ for a peak-to-peak ECG voltage of approximately 1 mV), and adds modified offset1 to the current sample. Modified offset1 is then added until its value equals 0. An application of this splicing function is illustrated in FIG. 6.

Validation Experiment

Employing the techniques of the foregoing present invention, a "validation" experiment was performed using similar sample data to that used in the experiment performed by Geddes and described in the above "background" section. The validation experiment was performed with a 1 Hz input voltage square wave with 0.2 second pulse duration period and 2 V peak-to-peak amplitude. A 1990Ω load resistor was used to limit the current transmitted to the subject. The resulting input and output voltages were passed through an analog low pass filter with a corner frequency of 400 kHz, sampled in an A/D converter at 1000 Hz with an input range of ±2.5 V, passed through a digital low pass filter with a corner frequency of 40 Hz, and decimated by 8 samples, respectively. The resulting resistance and capacitance values, $\overline{R'}$ and $\overline{C'}$, respectively, each based on the averaged mean of five measurements, were compared to results from Geddes' method, as follows:

| True Resistance (Ω) | Geddes' Apparent Impedance (Ω) | $\overline{R'}$ (Ω) | True Capacitance ($\mu$F) | $\overline{C'}$ ($\mu$F) |
|---|---|---|---|---|
| 50.4 | 105 | 47 | 50.6 | 51.2 |
| 502 | 90 | 503 | 50.6 | 50.8 |
| 999 | 105 | 1001 | 50.6 | 50.3 |

As can be observed, unlike Geddes' method, the invention provides a significantly accurate estimate of the resistance for a wide range of values. Further, for the first time, an estimate of the capacitance aspect of impedance is also provided. The mean error of the resistance measurements is −2%; the mean error of the capacitance measurements is +3%.

To determine a more valid estimation of a "typical" human transthoracic impedance, e.g., to replace previous invalid estimates that were based on the erroneous "pure resistance" assumption, the transthoracic impedance for 10 male and 10 female subjects was measured by employing the techniques of the present invention and by using the same parameters as were used in the above validation experiment. The following results were obtained:

| Gender | Age (yrs) | Wght (lbs) | R' | C' |
|---|---|---|---|---|
| Male | 36 ± 8 | 196 ± 33 | 1882 ± 634 | 35 ± 20 |
| Female | 33 ± 8 | 157 ± 37 | 2454 ± 1112 | 31 ± 17 |
| Combined | 34 ± 8 | 176 ± 39 | 2168 ± 929 | 33 ± 18 |

Using a statistical "t" test, the foregoing parameters and measured data between males and females were compared. Only weight was judged to be significantly different between genders (P≦0.011). Using linear regression, it was determined that the measured resistance and capacitance values were not significantly correlated with weight or age. To project a "mean" resistance and capacitance based on population, the sample statistics were extrapolated to general population statistics. Using 500 "simulation" groups for Monte Carlo simulations, the following population estimates were derived:

| Statistic | Population Resistance (Ω) | Population Capacitance ($\mu$F) |
|---|---|---|
| Mean | 1810 ± 164 | 37 ± 4 |
| Standard Deviation | 678 ± 231 | 19 ± 2 |

Based on these derived estimates, and assuming that cardiovascular disease does not significantly impact transthoracic impedance, a resistance of 2000Ω and capacitance of 40 $\mu$F much better typify transthoracic impedance of a human patient than a single 50Ω resistor.

Thus, preferred embodiments have been disclosed of methods and apparatus for estimating impedance, including electrode and transthoracic impedance in conjunction with non-invasive electrical cardiac therapy. While embodiments and applications of this invention have been shown and described, as would be apparent to those skilled in the art, many more modifications and applications are possible without departing from the inventive concepts herein. By way of example only, the aforedescribed ARMA model employing least squares estimation is considered just one preferred example of a combination mathematical model and parameter estimation technique. Given the teachings set forth herein, it would be apparent to one skilled in the art that other mathematical models and parameter estimation techniques, respectively, could be employed including, by way of non-limiting example only, a feed forward neural network with back propagation to obtain estimates of patient resistance. Similarly, many optimization techniques besides the aforedescribed preferred Powell's successive approximation method could be used to minimize the error between the observed and calculated decay to obtain an estimate of capacitance. Likewise, different algorithms may be substituted for the wavelet transform for ECG detection.

Further, while the aforedescribed preferred embodiments assume a resistor-capacitor series combination, given the teachings set forth herein, it would be apparent to one skilled in the art that a resistor-capacitor parallel combination or higher model order combinations, (e.g., more than one capacitor, etc.), combinations could be employed in accordance with the herein described underlying inventive concept of identifying the transfer function between the input and output voltages, respectively.

Moreover, while the aforedescribed impedance estimation methodology is described in conjunction with a defibrillation system—e.g., to measure the impedance of face-to-face electrodes or the transthoracic impedance of a patient—it is apparent that the inventive concepts could also be applied to estimate the impedance across any load.

The scope of the inventions, therefore, are not to be restricted except in the spirit of the appended claims.

What is claimed:

1. A method for estimating impedance, comprising the steps of:
    (1) applying a square wave input voltage, $V_{in}(t)$, across a load impedance to be measured in series with a selected resistance;
    (2) measuring a resulting output voltage, $V_{out}(t)$;
    (3) modeling the load impedance to be measured as a resistance component in series with a capacitance component;
    (4) estimating a first transfer function between $V_{in}(t)$ and $V_{out}(t)$ based on circuit analysis;
    (5) estimating a second transfer function between $V_{in}(t)$ and $V_{out}(t)$ based on a standard autoregressive moving average model; and
    (6) equating said first and second estimated transfer functions to derive an estimation of the respective resistance and capacitance components of the load impedance.

2. A method for estimating a load impedance, comprising the steps of:
    applying an input voltage $V_{in}(t)$ across the load in series with a selected resistance to derive an output voltage $V_{out}(t)$;
    estimating a first transfer function between $V_{in}(t)$ and $V_{out}(t)$ based on circuit analysis;

estimating a second transfer function between $V_{in}(t)$ and $V_{out}(t)$ based on a modelling technique; and equating the first and second estimated transfer functions to derive respective resistance and reactance components of the load impedance.

3. The method of claim 2, wherein a low current square wave voltage is used to supply $V_{in}(t)$ across the load.

4. The method of claim 3, wherein the low current square wave voltage used to supply $V_{in}(t)$ is applied across the load at a frequency of approximately 1–2 Hertz.

5. The method of claim 2, wherein the step of estimating a first transfer function between $V_{in}(t)$ and $V_{out}(t)$ based on circuit analysis is performed using the Laplace domain representation:

$$\frac{V_{out}(s)}{V_{in}(s)} = \frac{R + \frac{1}{sC}}{R + \frac{1}{sC} + R_1} \qquad (2)$$

where R represents the resistance component of the load impedance, C represents a capacitance that is inversely proportional to the reactance component of the load impedance, and $R_1$ is the selected resistance.

6. The method of claim 2, wherein the step of estimating a second transfer function between $V_{in}(t)$ and $V_{out}(t)$ based on a modelling technique is performed using an autoregressive moving average ("ARMA") model.

7. The method of claim 6, wherein ARMA model parameters are obtained using least squares estimation.

8. The method of claim 6, wherein the ARMA transfer function is calculated as $$V_{out}(k) = -a_1 V_{out}(k-1) + b_0 V_{in}(k) + b_1 V_{in}(k-1) \qquad (4).$$

9. The method of claim 6, wherein the reactance component of the load impedance is estimated by fitting a digitally sampled decay of $V_{out}(t)$ to estimate a capacitance that is inversely proportional to the reactance component.

10. The method of claim 9, wherein the capacitance is estimated by employing an optimization technique to minimize a squared error between observed and calculated decays of $V_{out}(t)$.

11. A method for selecting a defibrillation charge level to be delivered by a defibrillator to a patient over an electrode pair attached to the patient, comprising the following steps:

applying an input voltage across the electrodes in series with a selected resistance and measuring the resulting output voltage;

estimating a first transfer function between the input voltage and output voltage based on circuit analysis;

estimating a second transfer function between the input voltage and output voltage based on a modelling technique; and equating the first and second estimated transfer functions to derive respective resistance and reactance components of the combined patient and electrode impedance.

12. The method of claim 11, further comprising the step of selecting the defibrillation charge to be delivered to the patient based on the estimated resistance and reactance components of the combined patient and electrode impedance.

13. The method of claim 11, wherein a low current square wave voltage is used to supply the $V_{in}(t)$ across the load.

14. The method of claim 11, comprising the further step of isolating the defibrillator from the electrodes while applying the input voltage across the electrodes.

15. The method of claim 11, comprising the further step of isolating a patient monitor lead connected to the electrodes while applying the input voltage across the electrodes.

16. The method of claim 15, comprising the further step of sending a previously recorded patient signal over the patient monitor lead while the later is isolated from the electrodes.

* * * * *